(12) United States Patent
Uekita et al.

(10) Patent No.: US 10,596,221 B2
(45) Date of Patent: Mar. 24, 2020

(54) CONTROLLED-RELEASE FERTILIZER COMPRISING OXIDIZED GLUTATHIONE

(71) Applicant: Kaneka Corporation, Osaka (JP)

(72) Inventors: Ken Uekita, Hyogo (JP); Taku Mouri, Hyogo (JP); Toyoaki Watanabe, Hyogo (JP); Yu Fu, Hyogo (JP); Naoaki Taoka, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 113 days.

(21) Appl. No.: 15/671,721

(22) Filed: Aug. 8, 2017

(65) Prior Publication Data

US 2017/0333518 A1    Nov. 23, 2017

Related U.S. Application Data

(63) Continuation of application No. PCT/JP2016/053452, filed on Feb. 5, 2016.

(30) Foreign Application Priority Data

Feb. 9, 2015  (JP) ................................. 2015-023296

(51) Int. Cl.
| | |
|---|---|
| *A61K 38/06* | (2006.01) |
| *C05G 3/00* | (2020.01) |
| *C05F 11/10* | (2006.01) |
| *A01N 41/12* | (2006.01) |
| *A01N 25/12* | (2006.01) |
| *C07K 5/12* | (2006.01) |
| *C08B 11/12* | (2006.01) |

(52) U.S. Cl.
CPC ............ *A61K 38/063* (2013.01); *A01N 25/12* (2013.01); *A01N 41/12* (2013.01); *C05F 11/10* (2013.01); *C05G 3/0047* (2013.01); *C07K 5/123* (2013.01); *C08B 11/12* (2013.01)

(58) Field of Classification Search
None
See application file for complete search history.

(56) References Cited

U.S. PATENT DOCUMENTS

| | | | |
|---|---|---|---|
| 2004/0035162 A1* | 2/2004 | Williams | ................ C05B 17/00 71/28 |
| 2010/0016166 A1 | 1/2010 | Ogawa et al. | |
| 2010/0311837 A1 | 12/2010 | Sakai et al. | |
| 2014/0121100 A1 | 5/2014 | Habib et al. | |
| 2014/0194371 A1 | 7/2014 | Mouri et al. | |

FOREIGN PATENT DOCUMENTS

| | | |
|---|---|---|
| EP | 2103212 A1 | 9/2009 |
| EP | 2727932 A1 | 5/2014 |
| JP | H06-157181 A | 6/1994 |

(Continued)

OTHER PUBLICATIONS

International Search Report issued in International Application No. PCT/JP2016/053452; dated May 17, 2016 (2 pages).

(Continued)

*Primary Examiner* — Wayne A Langel
(74) *Attorney, Agent, or Firm* — Osha Liang LLP

(57) ABSTRACT

A controlled-release fertilizer includes oxidized glutathione and a release control agent, and a method produces the controlled-release fertilizer.

11 Claims, 4 Drawing Sheets

(56) References Cited

FOREIGN PATENT DOCUMENTS

| | | |
|---|---|---|
| JP | 2001-206792 A | 7/2001 |
| JP | 5452022 B2 | 3/2014 |
| WO | 2008/072602 A1 | 6/2008 |
| WO | 2009/099132 A1 | 8/2009 |
| WO | 2013/002317 A1 | 1/2013 |

OTHER PUBLICATIONS

Extended European Search Report issued in European Application No. 16749156.2, dated Aug. 1, 2018 (3 pages).

* cited by examiner

CONTROLLED-RELEASE FERTILIZER COMPRISING OXIDIZED GLUTATHIONE

TECHNICAL FIELD

One or more embodiments of the present invention relate to a controlled-release fertilizer comprising oxidized glutathione exerting useful activity on plants, such as plant growth promoting activity.

BACKGROUND

Glutathione is a peptide consisting of three amino acids, i.e., L-cysteine, L-glutamic acid, and glycine. Glutathione is present in a wide variety of living organisms including not only humans but also other animals, plants, and microorganisms, and it is an important compound for living organisms that is involved in, for example, removal of active oxygen species, detoxification, and amino acid metabolism.

Glutathione is present in vivo in the form of either reduced glutathione (N—(N-γ-L-glutamyl-L-cysteinyl)glycine) in which the thiol group of the L-cysteine residue is reduced in the form of SH (hereafter, it may be referred to as "GSH") or oxidized glutathione in which the thiol group of the L-cysteine residue is oxidized to form a disulfide bond between two glutathione molecules (hereafter, it may be referred to as "GSSG").

GSSG is known to be useful in the field of, for example, fertilizers, pharmaceuticals, and cosmetic products.

Patent Document 1 discloses that GSSG is useful as an active component of a plant growth regulator that increases the harvest index. For example, it has activity of increasing the number of seeds and the number of flowers of the plant or increasing the number of lateral shoots or tillers of a plant.

Patent Document 2 discloses that an ammonium salt, a calcium salt, or a magnesium salt of GSSG prepared by the production method under a specific heating condition is low in deliquescence and high in water solubility; that is, such salt is easy to handle.

Meanwhile, Patent Document 3 discloses that, in the presence of glutathione (GSH or GSSG) together with arginine and an organic acid, degradation of glutathione during storage can be inhibited, and storage stability is thus improved.

Patent Document 1: WO 2008/072602
Patent Document 2: WO 2013/002317
Patent Document 3: WO 2009/099132

SUMMARY

As disclosed in Patent Document 1, GSSG had heretofore been known to be effective as a fertilizer. However, the present inventors discovered that GSSG would be easily degraded and its effects on plants would not be sustained when it was actually applied as a fertilizer to soil.

Accordingly, one or more embodiments of the present invention enhance the stability of GSSG under the environment where GSSG is applied to plants, such as in soil, and provide a GSSG-containing fertilizer that can continuously exert useful effects of GSSG on plants.

One or more embodiments of the present invention are disclosed herein.

(1) A controlled-release fertilizer comprising GSSG and a release control agent.

(2) A method for producing the controlled-release fertilizer according to (1) comprising: a step of forming a mixture of the GSSG, the release control agent, and a medium, wherein the medium is water or a water-soluble medium; and a step of forming grains comprising the GSSG and the release control agent from the mixture.

The fertilizer of (1) can continuously exert its effects on plants since GSSG is less likely to be degraded under the environment where it is applied to plants.

The method of (2) enables production of the controlled-release fertilizer of (1) in which GSSG degradation is more effectively suppressed under the environment where it is applied to plants.

The term "fertilizer" used herein refers to a product to be applied to plants. The fertilizer according to one or more embodiments of the present invention can be used for supplying an active component at least comprising GSSG to plants. The fertilizer according to one or more embodiments of the present invention is a GSSG-containing composition to be applied to plants.

The term "controlled-release fertilizer" used herein refers to a product to be applied to plants, which is capable of controlled-release of an active component (at least comprising GSSG).

This description includes part or all of the content as disclosed in the description and/or drawings of Japanese Patent Application No. 2015-023296, which is a priority document of the present application.

According to one or more embodiments of the present invention, degradation of GSSG occurring under the environment where it is applied to plants, such as in soil, can be suppressed, and effects of such components on plants can be sustained.

DETAILED DESCRIPTION OF EMBODIMENTS

1. Oxidized Glutathione

Figure 1:
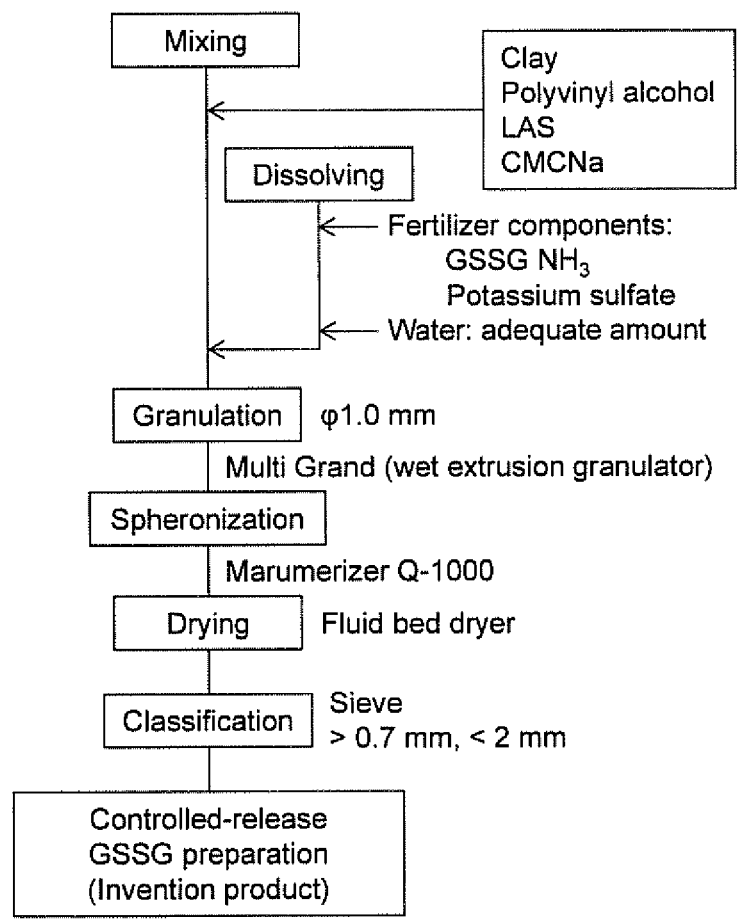
FIG. 1 shows a flow chart demonstrating a process of producing the GSSG-containing controlled-release fertilizer according to one or more embodiments of the present invention (hereafter, it is referred to as "the invention product").

Oxidized glutathione (GSSG) is a substance formed via a disulfide bond of two molecules of reduced glutathione (GSH, N—(N-γ-L-glutamyl-L-cysteinyl)glycine). The free form of oxidized glutathione (GSSG) is represented by the formula shown below.

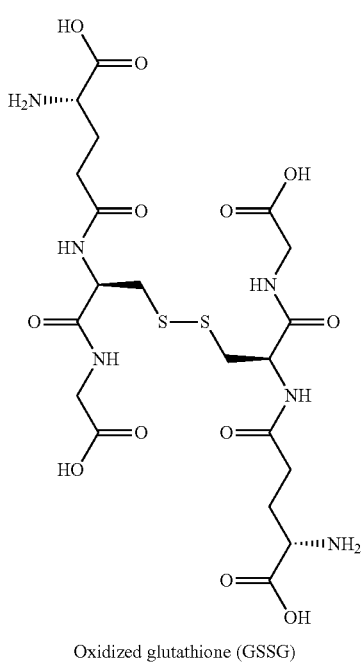 [SMILES: N[C@@H](CCC(=O)N[C@@H](CSSC[C@H](NC(=O)CC[C@H](N)C(=O)O)C(=O)NCC(=O)O)C(=O)NCC(=O)O)C(=O)O]

Oxidized glutathione (GSSG)

Various forms of oxidized glutathione (GSSG), such as free GSSG that is not bound to another substance and is not ionized, a salt formed of GSSG and an acid or base, a hydrate thereof and a mixture thereof, are within the scope of GSSG in one or more embodiments of the present invention. In addition, various forms of reduced glutathione (GSH), such as free GSH that is not bound to another substance and is not ionized, a salt formed of GSH and an acid or base, a hydrate thereof, and a mixture thereof, are within the scope of GSH in one or more embodiments of the present invention.

The fertilizer of one or more embodiments of the present invention may comprise reduced glutathione. The content of oxidized glutathione in the fertilizer may be relatively larger than that of reduced glutathione. The fertilizer may comprise substantially no reduced glutathione. The total mass of oxidized glutathione (wherein the mass is expressed in terms of its free form) may be 70% by mass or more, 80% by mass or more, 90% by mass or more, 95% by mass or more, 98% by mass or more, or 100% by mass, relative to the total mass of oxidized glutathione and reduced glutathione contained in the fertilizer of one or more embodiments of the present invention (wherein the mass is expressed in terms of their free forms).

A GSSG salt is not particularly limited, provided that it is at least one salt acceptable as a fertilizer, such as an ammonium salt, a calcium salt, a magnesium salt, a sodium salt, or a lithium salt, and at least one salt may be selected from an ammonium salt, a calcium salt, and a magnesium salt. As disclosed in Patent Document 2, an ammonium salt, a calcium salt, and a magnesium salt of GSSG in the solid state are low in deliquescence, easy to handle, and highly soluble in water. Thus, such salts may be used. As described in Patent Document 2, such salts can be obtained in the solid form by heating GSSG to 30° C. or higher while keeping it in contact with an aqueous medium selected from water and/or water-soluble media in the presence of a substance capable of generating at least one type of cation selected from the ammonium ion, the calcium cation, and the magnesium cation. A heating temperature is not particularly limited, provided that it may be 30° C. or higher, 33° C. or higher, 35° C. or higher, or 40° C. or higher. While the upper limit is not particularly limited, for example, it may be 80° C. or lower, 70° C. or lower, or 60° C. or lower. In the case of industrial-scale production, a temperature range of 53° C. to 60° C. may be used. The aqueous medium may be used alone or two or more media may be used in adequate combination. Water in combination with a water-soluble medium may be used. In such a case, water functions as a good medium of oxidized glutathione and a water-soluble medium functions as a poor medium. The volume of the water-soluble medium may be, for example, approximately 1 to 1,000 parts by volume, approximately 5 to 500 parts by volume, approximately 10 to 100 parts by volume, or approximately 12 to 50 parts by volume, relative to 10 parts of water by volume. Examples of the water-soluble media that can be used include an alcohol (e.g., methanol, ethanol, propanol, butanol, and ethylene glycol) and a ketone (e.g., acetone and methyl ethyl ketone). Examples of GSSG salts obtained by such method include 1 ammonium salt of GSSG, a 0.5 calcium salt of GSSG, 1 calcium salt of GSSG, a 0.5 magnesium salt of GSSG, and 1 magnesium salt of GSSG.

2. Controlled-Release Fertilizer 2.1. Forms of Controlled-Release Fertilizer

The controlled-release fertilizer according to one or more embodiments of the present invention can be in any of various forms of controlled-release preparations, such as a controlled-release solid preparation comprising GSSG dispersed in a solid matrix, a controlled-release coated preparation comprising a GSSG-containing preparation (it may be the controlled-release solid preparation) provided with a coat layer, or a controlled-release emulsion preparation comprising GSSG-containing grains emulsified and dispersed as a disperse phase therein. The controlled-release fertilizer according to one or more embodiments of the present invention may be in the form of a controlled-release solid preparation. A controlled-release solid preparation provided with a coat layer is within the scope of the controlled-release fertilizer according to one or more embodiments of the present invention.

2.2. Release Control Agent and Other Components

In one or more embodiments of the present invention, the term "release control agent" refers to a substance that is capable of imparting GSSG with a controlled-release property, and an adequate substance is selected in accordance with the relevant controlled-release preparation. In the case of a controlled-release solid preparation, for example, a release control agent may be used as at least one component of a solid matrix. In the case of a controlled-release coated preparation, a release control agent may be used as at least one component constituting a coat layer. In the case of a controlled-release emulsion preparation, a release control agent may be used as at least one component selected from a component contained in a dispersion phase, a component contained in an interface between a dispersion phase and a continuous phase, and a component contained in a continuous phase.

A release control agent may be at least a substance selected from among a thickener, a binder, and an adsorptive carrier. While such release control agent can be used in any form of the controlled-release fertilizers described above, at least one component may constitute a solid matrix of a controlled-release solid preparation, at least one component may constitute a coat layer of the controlled-release coated preparation, or at least one component may be contained in a dispersion phase of the controlled-release emulsion preparation. At least one component may constitute the solid matrix of the controlled-release solid preparation or at least one component may constitute the coat layer of the controlled-release coated preparation. At least one component may constitute the solid matrix of the controlled-release solid preparation.

A thickener and a binder cannot be exclusively classified from each other, and some materials have functions of both the thickener and the binder. In this description, accordingly, a material having a function of either a thickener or binder is referred to as "a thickener and/or a binder" for the convenience of description. In one or more embodiments of the present invention, "at least one substance selected from a thickener, a binder, and an adsorptive carrier" can also be expressed as "at least one substance selected from materials as a thickener and/or binder and an adsorptive carrier."

Examples of thickeners and/or binders that are useful as release control agents include: polymeric compounds, such as carboxymethyl cellulose, methyl cellulose, ethyl cellulose, polyvinyl pyrrolidone, pullulan, acrylic acid-based polymer, polyvinyl alcohol, gelatin, agar, gum arabic, gum arabic powder, xanthan gum, trant gum, guar gum, gellan gum, locust bean gum, partially pregelatinized starch, macrogol, starch, soluble starch, dextrin, tragacanth gum, β-glucan, pectin, casein, soybean protein, hydroxyethyl cellulose, acetylcellulose, lignin sulfonic acid, carboxymethyl starch, hydroxyethyl starch, polyvinyl methyl ether, hydroxypropyl cellulose, hydroxypropyl methyl cellulose, polyethylene glycol, polyethylene oxide, polyvinylpyrrolidone, shellac, rosin, tall oil, ester gum, polyvinyl acetate, polylactic acid, polyvinyl chloride, polyester, polyurea, polyamide, cumarone resin, biodegradable polymers, paraffin wax, microcrystalline wax, petrolatum, montan wax, carnauba wax, cotton wax, beeswax, wool wax, non-ionic polymeric surfactant, anionic polymeric surfactant, cationic polymeric surfactant, amphoteric polymeric surfactant, and alginic acid; non-polymeric compounds, such as sodium silicate, glycerin, vegetable and animal oils, fat and oil, liquid paraffin, fuel oil, glucose, sucrose, mannitol, sorbitol, non-polymeric non-ionic surfactant, non-polymeric anionic surfactant, non-polymeric cationic surfactant, and non-polymeric amphoteric surfactant; and salts thereof that are acceptable as fertilizers. At least one type of substance selected from the group consisting of the above can be used. Thickeners and/or binders may be made of polymeric compounds, and examples thereof include carboxymethyl cellulose, a salt thereof, polyvinyl alcohol, starch, gum arabic, hydroxyethyl cellulose, lignin sulfonic acid, a salt thereof, and polyethylene glycol. Examples of carboxymethyl cellulose salts include: alkali metal salts, such as sodium, potassium, and lithium salts; and alkaline earth metal salts, such as magnesium and calcium salts. Carboxymethyl cellulose and salts thereof have excellent release control capacities and exert acidic to neutral properties. Accordingly, such substances may be used for GSSG stabilization.

Examples of adsorptive carriers useful as release control agents include inorganic and organic porous materials.

As inorganic porous materials, one or more substances selected from, for example, clay, diatomaceous earth, zeolite, pearlite, zeeklite, sericite, kaolin, pumice, silica, vermiculite, calcium carbonate, and activated clay can be used. Clay may be used as an inorganic porous material. Since clay is acidic to neutral in water, it contributes to GSSG stabilization.

Examples of organic porous materials that can be used include dried plant materials of rice hull, sawdust, soybean meal, corn stem, and plant fiber, pulp flock, white carbon, and active carbon.

In addition to the substances described above, the controlled-release fertilizer according to one or more embodiments of the present invention can adequately comprise other components acceptable as the fertilizers, such as water, other fertilizer components, and excipients such as lactose and cellulose.

Examples of other fertilizer components include elements that are useful as fertilizers, such as potassium, urea, phosphorus, calcium, and magnesium. The controlled-release fertilizer according to one or more embodiments of the present invention can comprise a substance that is capable of supplying the other fertilizer components, such as potassium sulfate that supplies potassium.

2.3. Composition of Controlled-Release Fertilizer

The composition of the controlled-release fertilizer according to one or more embodiments of the present invention is not particularly limited. The oxidized glutathione content may be 0.000001% by mass or more (or 0.005% by mass or more) to 20% by mass or less (or 5% by mass or less), relative to the total amount of the controlled-release fertilizer.

When the controlled-release fertilizer according to one or more embodiments of the present invention comprises a thickener and/or a binder as a release control agent, the content of the thickener and/or the binder may be 0.01% by mass or more (or 0.1% by mass or more) to 20% by mass or less (or 10% by mass or less), relative to the total amount of the controlled-release fertilizer. Such content may be used when the thickener and/or the binder comprise a polymeric compound, or when the polymeric compound is carboxymethyl cellulose or a salt thereof.

When the controlled-release fertilizer according to one or more embodiments of the present invention comprises an adsorptive carrier as a release control agent, the content of the adsorptive carrier may be 60% by mass or more (or 80% by mass or more) to 99.98% by mass or less (or 99% by mass or less), relative to the total amount of the controlled-release fertilizer. Such content may be used when the adsorptive carrier is an inorganic porous material.

The controlled-release fertilizer according to one or more embodiments of the present invention may comprise at least one thickener and/or binder and an adsorptive carrier as a release control agent. In such a case, grains of the adsorptive carrier easily form a matrix by binding to each other via the at least one thickener and/or binder. Such matrix can comprise oxidized glutathione dispersed therein.

When the controlled-release fertilizer according to one or more embodiments of the present invention comprises a plurality of components as thickeners and/or binders, the amount of such components may be within the range described above, and the total amount of the thickeners and/or the binders may be within the range described above. When the controlled-release fertilizer according to one or more embodiments of the present invention comprises a plurality of types of components as adsorptive carriers, the amount of such components may be within the range described above, and the total amount of the adsorptive carriers may be within the range described above. The same applies to the contents according to one or more embodiments described below.

The controlled-release fertilizer according to one or more embodiments of the present invention comprises 0.000001% to 20% by mass of oxidized glutathione, 0.01% to 20% by mass of a thickener and/or a binder (e.g., a polymeric compound, carboxymethyl cellulose or a salt thereof), and 60% to 99.98% by mass of an adsorptive carrier (e.g., an inorganic porous material). According to one or more embodiments of the present invention, the controlled-release fertilizer comprises 0.005% to 5% by mass of oxidized glutathione, 0.1% to 10% by mass of a thickener and/or a binder (e.g., a polymeric compound, carboxymethyl cellulose or a salt thereof), and 80% to 99% by mass of an adsorptive carrier (e.g., an inorganic porous material).

The controlled-release fertilizer according to one or more embodiments of the present invention may or may not comprise water as described above, and the water content may be 10% by mass or less, 8% by mass or less, or 5% by mass or less, relative to the total amount of the controlled-release fertilizer. When the water content is within such range, GSSG stability is further enhanced.

The contents of the components described above may be used when the controlled-release fertilizer according to one or more embodiments of the present invention is in the form of a controlled-release solid preparation.

The controlled-release fertilizer according to one or more embodiments of the present invention may have a pH level of from 2.0 to less than 8.0 when dispersed in water, such pH level may be 7.0 or less, or 6.5 or less. GSSG stability of a fertilizer composition exhibiting a pH level within such range is further enhanced. When GSSG is released from the controlled-release fertilizer according to one or more embodiments of the present invention into water surrounding the fertilizer, GSSG can be stably present in the water. The pH level is measured by adding 3 g of the controlled-release fertilizer according to one or more embodiments of the present invention to 100 ml of distilled water, dispersing the fertilizer thoroughly, and then measuring the pH level at 25° C.

2.4. Controlled-Release Property

The controlled-release fertilizer according to one or more embodiments of the present invention may have the controlled-release properties as described below.

1.25 g of the controlled-release fertilizer according to one or more embodiments of the present invention is added to 25 ml of distilled water and the resultant is allowed to stand at 30° C., and the initial total mass of GSSG in the controlled-release fertilizer (i.e., the total mass expressed in terms of a free form of GSSG, the same applies hereinbelow) is designated as "T." Under such circumstances, the total mass of GSSG eluted into water (as described above) is 0.60 T or less, or 0.50 T or less after 12 hours, 0.80 T or less, or 0.75 T or less after 24 hours, 0.90 T or less, or 0.85 T or less after 48 hours, and 0.95 T or less, or 0.90 T or less after 72 hours. While the lower limit of the amount of elution is not particularly limited, under the conditions described above, it is 0.20 T or more, or 0.30 T or more after 12 hours, it is 0.50 T or more, or 0.60 T or more after 24 hours, it is 0.60 T or more, or 0.70 T or more after 48 hours, and it is 0.70 T or more, or 0.80 T or more after 72 hours.

The fertilizer of one or more embodiments of the present invention having the controlled release properties as described above is capable of controlled release of GSSG while stably retaining GSSG over a sufficiently long period of time.

3. Method of Production

A method for producing the controlled-release fertilizer according to one or more embodiments of the present invention is not particularly limited.

When the controlled-release fertilizer according to one or more embodiments of the present invention is a controlled-release solid preparation, a method of production may comprise:

a step of mixing comprising forming a mixture of GSSG, a release control agent, and a medium, wherein the medium is water or a water-soluble medium; and a step of granulation comprising forming grains comprising the GSSG and the release control agent from the mixture.

The step of mixing may comprise dissolving GSSG in an adequate amount of a medium and mixing the resulting solution with a release control agent and other components. In the step of mixing, GSSG dissolved in the medium may be thoroughly dispersed in a phase comprising a release control agent. When the release control agent contains an adsorptive carrier, at least a part of GSSG dissolved in the medium may be dispersed while adsorbed to the adsorptive carrier.

The amount of a medium used in the step of mixing is not particularly limited, and the amount of water to be used may be adequately determined, so as to obtain a sufficiently homogeneous mixture. As the water-soluble medium, an alcohol, such as ethanol, can be used. A medium may be water or a medium mixture comprising water and an alcohol.

A mixture formed in the step of mixing may be in a paste or liquid state.

The step of granulation may be carried out in accordance with a conventional technique of granulation, such as wet extrusion granulation. The step of granulation can comprise a step of spheronization or a step of drying, according to need. In the step of drying, the medium is removed by evaporation, and a matrix comprising a release control agent retains GSSG dispersed therein. When the release control agent comprises an adsorptive carrier, at least a part of GSSG may be dispersed while adsorbed to the adsorptive carrier.

The configuration and the dimension of the grains of the controlled-release fertilizer according to one or more embodiments of the present invention obtained by the step of granulation are not particularly limited. From the viewpoint of operability and controlled-release properties, the configuration thereof may be spherical or cylindrical, and the dimension thereof may be 0.01 cm or more, 0.05 cm or more, or 0.1 cm or more, to 10 cm or less, 5 cm or less, or 2 cm or less, in terms of the maximal dimension of each grain. The minimal dimension of each grain can be within the same range.

4. Target Plants

Target plants to which the controlled-release fertilizer according to one or more embodiments of the present invention is to be applied are not particularly limited, and examples thereof include various plants, such as dicotyledons and monocotyledons.

Examples of dicotyledons to which the controlled-release fertilizer according to one or more embodiments of the present invention is to be applied include plants of *Pharbitis, Convolvulus, Ipomoea, Cuscula, Dianthus, Stellaria, Minuartia, Cerastium, Sagina japonica, Arenaria, Moehringia, Pseudostellaria, Honkenya, Spergula, Silene, Lychnis, Silene firma, Caryophyllaceae, Casuarinaceae, Saururaceae, Piperaceae, Chloranthaceae, Salicaceae, Myricaceae, Juglandaceae, Betulaceae, Fagaceae, Ulmaceae, Moraceae, Urticaceae, Podostemaceae, Proteaceae, Olacaceae, Santalaceae, Loranthaceae, Aristolochiaceae, Rafflesiaceae, Balanophoraceae, Polygonaceae, Chenopodiaceae, Amaranthaceae, Nyctaginaceae, Theligonaceae,*

*Phiytolaccaceae, Aizoaceae, Portulacaceae, Magnoliaceae, Trochodendraceae, Cercidiphyllaceae, Nymphaeaceae, Ceratophyllaceae, Ranunculaceae, Lardizabalaceae, Berberidaceae, Menispermaceae, Calycanthaceae, Lauraceae, Papaveraceae, Capparaceae, Brassicaceae, Droseraceae, Nepenthaceae, Crassulaceae, Saxifragaceae, Pittosporaceae, Hamamelidaceae, Platanaceae, Rosaceae, Leguminosae, Oxalidaceae, Geraniaceae, Linaceae, Zygophyllaceae, Rutaceae, Simaroubaceae, Meliaceae, Polygalaceae, Euphorbiaceae, Callitrichaceae, Buxaceae, Empetraceae, Coriariaceae, Anacardiaceae, Aquifoliaceae, Celastraceae, Staphyleaceae, Icacinaceae, Aceraceae, Hippocastanaceae, Sapindaceae, Sabiaceae, Balsaminaceae, Rhamnaceae, Vitaceae, Elaeocarpaceae, Tiliaceae, Malvaceae, Sterculiaceae, Dilleniaceae, Theaceae, Guttiferae, Elatinaceae, Tamaricaceae, Violaceae, Flacourtiaceae, Stachyuraceae, Passifloraceae, Begoniaceae, Cactaceae, Thymelaeaceae, Elaeagnaceae, Lythraceae, Punicaceae, Rhizophoraceae, Alangiaceae, Melastomataceae, Trapaceae, Onagraceae, Haloragaceae, Hippuridaceae, Araliaceae, Umbellferae, Cornaceae, Diapensiaceae, Clethraceae, Pyrolaceae, Ericaceae, Myrsinaceae, Primulaceae, Plumbaginaceae, Ebenaceae, Symplocaceae, Styracaceae, Oleaceae, Buddlejaceae, Gentianaceae, Apocynaceae, Asclepiadaceae, Polemoniaceae, Boraginaceae, Verbenaceae, Lamiaceae, Solanaceae, Scrophulariaceae, Bignonlaceae, Pedaliaceae, Orobanchaceae, Gesneriaceae, Lentibulariaceae, Acanthaceae, Myoporaceae, Phrymaceae, Plantaginaceae, Rubiaceae, Caprifoliaceae, Adoxaceae, Valerianaceae, Dipsacaceae, Cucurbitaceae, Campanulaceae,* and *Asteraceae.*

Examples of monocotyledons to which the controlled-release fertilizer according to one or more embodiments of the present invention is to be applied include plants of *Spirodela, Lemna, Cattleya, Cymbidium, Dendrobium, Phalaenopsis, Vanda, Paphiopedilum, Orchidaceae, Typhaceae, Sparganiaceae, Potamogetonaceae, Najadaceae, Scheuchzeriaceae, Alismataceae, Hydrochariaceae, Triuridaceae, Gramineae, Cyperaceae, Palmae, Araceae, Eriocaulaceae, Commelinaceae, Pontederiaceae, Juncaceae, Stemonaceae, Lliaceae, Amaryllidaceae, Dioscoreacea, Iridaceae, Musaceae, Zingiberaceae, Cannaceae,* and *Burmanniaceae.*

Target plants are not limited to wild-type plants, and mutants, transformants, and the like may be the targets.

5. Method of Application

A method of application of the controlled-release fertilizer according to one or more embodiments of the present invention to plants are not particularly limited, provided that the controlled-release fertilizer according to one or more embodiments of the present invention or GSSG released from the controlled-release fertilizer according to one or more embodiments of the present invention can be brought into contact with a plant body, such as the root, the stem, the leaf, and the like of the target plants. The controlled-release fertilizer according to one or more embodiments of the present invention may be brought into direct contact with the plant body, or the controlled-release fertilizer according to one or more embodiments of the present invention may be applied to a cultivation support, such as soil, where the plant is rooted. When the controlled-release fertilizer according to one or more embodiments of the present invention is applied to a cultivation support, such as soil, that surrounds a plant root, GSSG can be stably supplied to the plant root over a long period of time. Accordingly, such application may be used. It should be noted that a method of application of the controlled-release fertilizer according to one or more embodiments of the present invention to plants is not particularly limited, as described above.

The controlled-release fertilizer according to one or more embodiments of the present invention can be applied to plants at any stage of plant cultivation without particular limitation in terms of the timing of application. Such fertilizer may be applied at one or more stages selected from seeding, rearing of seedlings, settlement, and additional fertilization. The fertilizer may be applied at each stage of seeding, rearing of seedlings, settlement, and additional fertilization.

EXAMPLES

Hereafter, one or more embodiments of the present invention are described with reference to specific examples, although the technical scope of one or more embodiments of the present invention is not limited to these examples. It should be noted that GSSG used in the following examples does not contain reduced glutathione.

Example 1: Production of Controlled-Release Oxidized Glutathione Preparation (the Invention Product)

1. Composition of Raw Materials

The composition of raw materials of the controlled-release oxidized glutathione preparation (i.e., the invention product) was as described below. GSSG in the form of an ammonium salt was used. The proportions of GSSG incorporated shown in Tables 1 and 2 are in terms of the salt form as described above.

TABLE 1

| Composition | Proportion (wt %) | Weight (g) |
|---|---|---|
| Ammonium salt of oxidized glutathione (GSSG NH$_3$) (Kaneka Corporation) | 1 | 6 |
| Potassium sulfate (Mitsui & Co. Ltd.) | 0.3 | 2 |
| Clay (Showa KDE Co. td.) | 95.4 | 572 |
| Polyvinyl alcohol (Denka Co., Ltd.) | 2 | 12 |
| Linear alkylbenzene sulfonate sodium (LAS) (Lion Corporation) | 0.3 | 2 |
| Carboxymethyl cellulose sodium (CMCNa) (Dai-ichi Kogyo Seiyaku Co., Ltd.) | 1 | 6 |
| Total | 100 | 600 |

2. Process of Granulation

In accordance with the procedure shown in FIG. 1, the invention product in the granular form was produced.

At the outset, clay, polyvinyl alcohol, linear alkylbenzene sulfonate, and carboxymethyl cellulose sodium of the weights shown in Table 1 were mixed to obtain a mixture. Separately, an ammonium salt of oxidized glutathione and potassium sulfate of the weights shown in Table 1 were dissolved in an adequate amount (about 114 ml) of water to obtain a solution.

The solution was mixed with the mixture, and the resultant was subjected to wet extrusion granulation with the use of a wet extrusion granulator (Multi Grand, Dalton Corporation) to form cylindrical grains with the diameter of 1.0 mm and the length of about 1 to 20 mm.

Subsequently, the cylindrical grains were spheronized with the use of a spheronizer (Marumerizer Q-1000, Dalton Corporation) and then dried with the use of a fluid bed dryer. Thereafter, grains were classified with the use of a sieve and 558 g of cylindrical grains with the length of over 0.7 mm to less than 2 mm were obtained (yield: 93%). The resultant was used as "the invention product" for the following experiment. The pH level measured at 25° C. when 3 g of the invention product was thoroughly dispersed in 100 ml of distilled water was 5.

Comparative Example 1: Production of Release-Uncontrolled Preparation of Oxidized Glutathione (the Comparative Product)

1: Composition of Raw Materials

The composition of raw materials of a release-uncontrolled preparation of oxidized glutathione (i.e., the comparative product) is as described below.

TABLE 2

| Composition | Proportion (wt %) | Weight (g) |
| --- | --- | --- |
| Ammonium salt of oxidized glutathione (GSSG NH$_3$) (Kaneka Corporation) | 1 | 6 |
| Potassium sulfate (Mitsui & Co. Ltd.) | 0.3 | 2 |
| Lactose monohydrate (Wako Pure Chemical Industries Ltd.) | 98.7 | 592 |
| Total | 100 | 600 |

2. Process of Granulation

Figure 2:
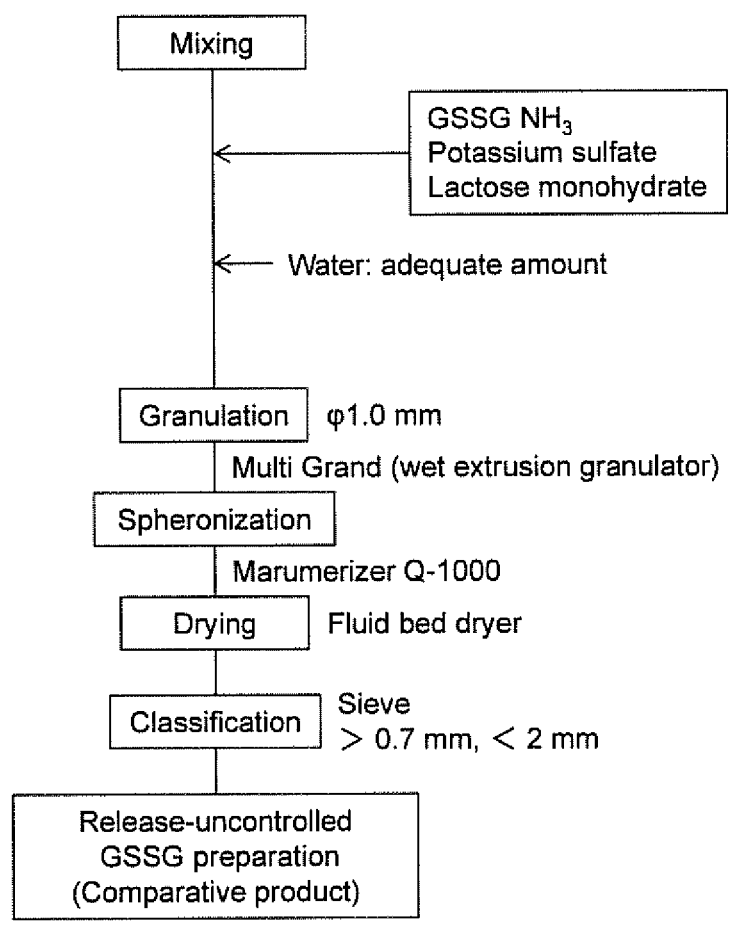
FIG. 2 shows a flow chart demonstrating a process of producing a GSSG-containing release-uncontrolled fertilizer (hereafter, it is referred to as "the comparative product").

In accordance with the procedure shown in FIG. 2, the comparative product in the granular form was produced.

At the outset, oxidized glutathione, potassium sulfate, and a lactose monohydrate of the weights shown in Table 2 were mixed, and an adequate amount (about 40 ml) of water was further added. The resulting mixture was subjected to wet extrusion granulation with the use of a wet extrusion granulator (Multi Grand, Dalton Corporation) to form cylindrical grains with the diameter of 1.0 mm and the length of about 1 to 20 mm.

Subsequently, the cylindrical grains were spheronized with the use of a spheronizer (Marumerizer Q-1000, Dalton Corporation) and then dried with the use of a fluid bed dryer. Thereafter, grains were classified with the use of a sieve and 503 g of cylindrical grains with the length of over 0.7 mm to less than 2 mm were obtained (yield: 84%). The resultant was used as "the comparative product" for the following experiment.

Example 2: Confirmation of Elution Behavior of Oxidized Glutathione from the Controlled-Release Oxidized Glutathione Preparation 1. Method of Testing The invention product and the comparative product were evaluated in terms of eluting properties of oxidized glutathione in water in the manner described below.

Distilled water (25 ml) and 1.25 g of the invention product or the comparative product were introduced into a 50-ml centrifuge tube (Iwaki). The invention product or the comparative product (1.25 g) comprises 12.2 mg of oxidized glutathione (in terms of the free form). The mixture was allowed to stand in an incubator at 30° C. for 72 hours at a maximum. The amount of oxidized glutathione eluted in an aqueous phase in the centrifuge tube was measured via HPLC immediately after mixing (0 hours after the initiation of storage), 4 hours after the initiation of storage, 24 hours after the initiation of storage, 48 hours after the initiation of storage, and 72 hours after the initiation of storage. The proportion of the amount of oxidized glutathione eluted into the aqueous phase relative to the amount of oxidized glutathione contained in the invention product or the comparative product introduced into the centrifuge tube was designated as the elution ratio (%). The amount of oxidized glutathione was measured in terms of the free form. The invention product and the comparative product were each subjected to the measurement described above by preparing samples for each measurement time point.

2. Results

Figure 3:
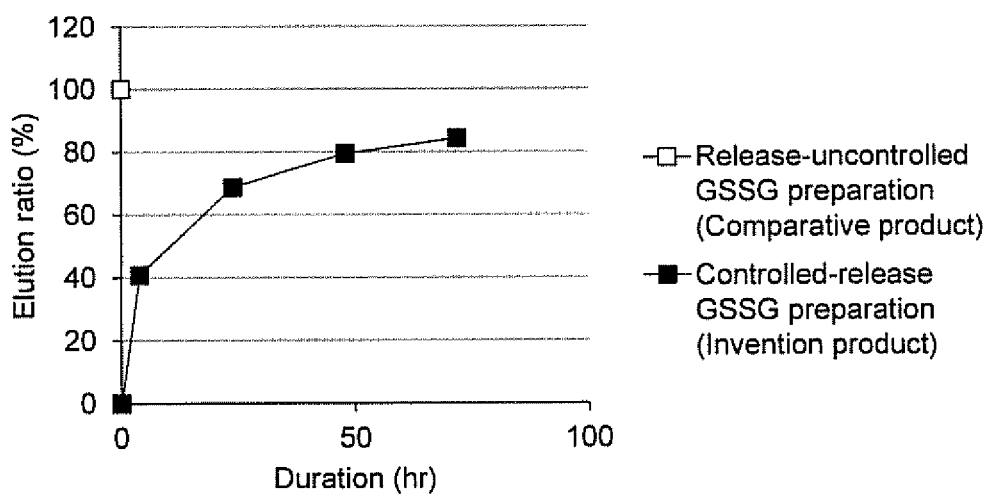
FIG. 3 shows a chart demonstrating GSSG-releasing properties of the invention product and of the comparative product in water.

The results are shown in FIG. 3. When the comparative product was mixed with distilled water, all oxidized glutathiones were eluted immediately thereafter. In the case of the invention product, however, it was confirmed that oxidized glutathione was gradually eluted into water.

Example 3: Confirmation of Stability of the Controlled-Release Oxidized Glutathione Preparation in Soil 2. Test Method Stability of the invention product and the comparative product in soil was confirmed in the manner described below.

Fine-grained gray lowland soil sampled from the field was used as soil.

The test group subjected to the stability test of the invention product was designated as T1 and the test group subjected to the stability test of the comparative product was designated as T2.

The soil (50 g) and 0.3 g of the invention product or the comparative product were introduced into a pot (width×depth×height=7 cm×7 cm×5 cm), and 4.4 g of water was added thereto so as to adjust the moisture content of the soil to about 40%. Thereafter, the pot was stored in an incubator maintained at 25° C. for up to 7 days. During the storage in the incubator, an adequate amount of water was added upon evaporation of the moisture. The samples of the invention product and of the comparative product to be subjected to analysis were prepared, so that the residual ratio of oxidized glutathione in soil could be measured in the manner described below immediately after mixing (0 hours after the initiation of storage), 3 days after the initiation of storage, 5 days after the initiation of storage, and 7 days after the initiation of storage.

The residual ratio of oxidized glutathione in soil was measured in the manner described below.

A pot full of the soil sample to be subjected to each measurement and 100 ml of a 1 M HCl aqueous solution were added to a 200-ml beaker, and the content of the beaker was agitated for 30 minutes to allow oxidized glutathione to elute from the soil. Subsequently, about 10 ml of 10 M NaOH was added thereto to neutralize the sample, followed by filtration. The filtrate was concentrated under a reduced pressure with the use of an evaporator (water bath temperature: about 40° C.) to adjust the volume thereof to about 10 ml. The concentrate was introduced into a measuring flask, and the amount of the content was adjusted to 20 ml with the addition of water to obtain an aqueous sample solution. The concentration of oxidized glutathione in the aqueous sample solution was measured via HPLC. The proportion of the amount of oxidized glutathione in the aqueous sample solution relative to the amount of oxidized glutathione in the invention product or the comparative product contained in each pot was designated as the residual ratio (%). The concentration and the amount of oxidized glutathione were expressed in terms of the free form.

2. Results

Figure 4:
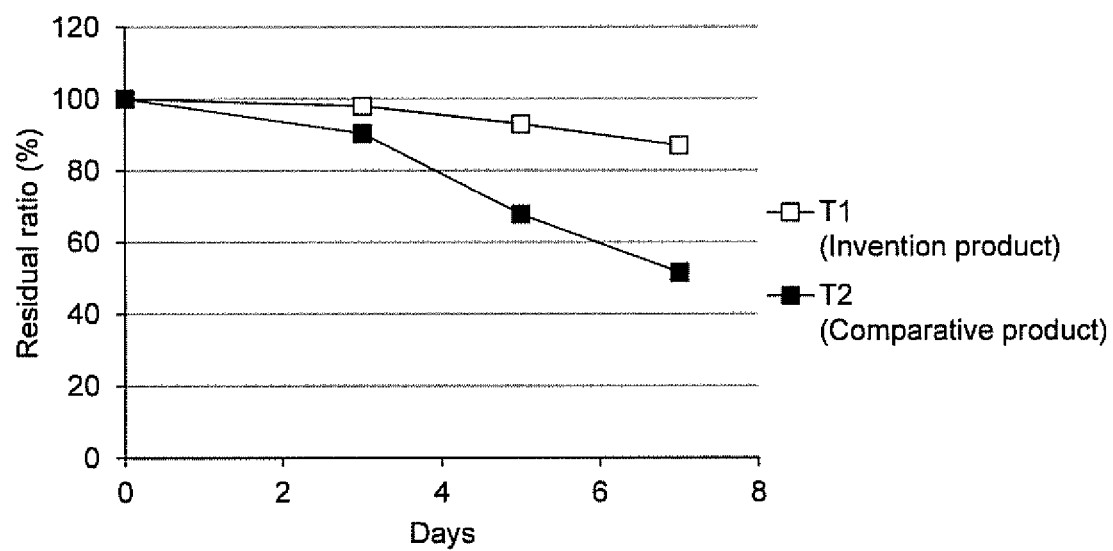
FIG. 4 shows a chart demonstrating a change with the elapse of time in the GSSG residual ratio when the invention product and the comparative product are mixed with soil.

The residual ratio of oxidized glutathione (%) at each point of the measurement is shown in Table 3 and FIG. 4.

TABLE 3

| Test group | Number of days | | | |
|---|---|---|---|---|
| | 0 | 3 | 5 | 7 |
| T1 (Invention product) | 100 | 98 | 93 | 87 |
| T2 (Comparative Product) | 100 | 90 | 68 | 52 |

The residual ratio of oxidized glutathione in T1 (the invention product) was 87% (the degradation rate: 13%) 7 days after the initiation of storage of the soil. Meanwhile, the residual ratio of oxidized glutathione in T2 (the comparative product) was 52% (the degradation rate: 48%). It was thus confirmed that stability of oxidized glutathione in soil would be enhanced to a significant extent by preparing oxidized glutathione in the form of a controlled-released preparation as with the case of the invention product. This indicates that oxidized glutathione prepared in the form of a controlled-released preparation can inhibit degradation such as biodegradation.

Example 4: Confirmation of Plant Growth Promoting Effects

1. Test Method

Seedlings of *Brassica chinensis komatsuna* (Takii Co., Ltd.) were raised under the conditions described below. When the seedling raising test was initiated, 3.7 g of the comparative product or the invention product was added and mixed into the soil, so as to adjust the amount of oxidized glutathione (in terms of the free form) to 36 mg per pot. Concerning a control test group, 3.7 g of clay was added and mixed into the soil as a blank sample, when the seedling raising test was initiated.
Duration: 6 weeks
Place: Plant cultivation incubator
Culture soil: Propagation soil (Takii Co., Ltd.), vermiculite
Temperature: 20° C.
Light: 115 μmol m$^{-2}$ s$^{-1}$ (10,000 lux) (light: 12 hours; dark: 12 hours)
Test groups: Control; comparative product; invention product
Number of samples: 3 strains/group
Pot size (width×depth×height): 7 cm×7 cm×5 cm The leaf length and the weight of the terrestrial part were measured 6 weeks later.

2. Results

The results are shown in Table 4.

TABLE 4

| | | Test groups | | | |
|---|---|---|---|---|---|
| Item | | Control | Comparative product | Invention product | Effects |
| GSSG amount | (mg/pot) | — | 36 | 36 | — |
| Leaf length | (mm) | 110 | 112 | 140 | Increased |
| Weight of terrestrial part | (g) | 3.4 | 3.6 | 5.0 | Increased |

It was confirmed that the use of the invention product would promote the plant growth to a significant extent.

Example 5: Confirmation of Influence of Moisture Content of the Controlled-Release Oxidized Glutathione Preparation on Storage Stability 1. Test Method The influence of the moisture content of the invention product on the storage stability was evaluated in the manner described below.

The moisture content of the invention product was 1% by mass. Moisture content was determined by subjecting 5 g each of the preparations to the measurement with the use of an infrared moisture gauge (Kett Electric Laboratory) at 110° C. for 15 minutes.

The invention product (10.0 g; moisture content: 1% by mass) was introduced into an aluminum-laminated bag (Lamizip, AL-9) and the bag was hermetically heat-sealed. The bag was not deaerated at the time of sealing. Also, 10.0 g each of the invention products were introduced into aluminum-laminated bags, and distilled water was further added to adjust the moisture content of the invention product to 8% by mass, 10% by mass, and 15% by mass, respectively, and the bags were then hermetically heat-sealed. The samples were allowed to stand in an incubator at 60° C. for 1 week, and the amount of oxidized glutathione in the invention product after storage was measured via HPLC. The proportion of the amount of oxidized glutathione contained in the invention product after storage relative to the amount of oxidized glutathione contained in the invention product immediately before the test was designated as the residual ratio (%).

2. Results

The results are shown in Table 5.

TABLE 5

| | Moisture content of invention product | | | |
|---|---|---|---|---|
| Item | 1% by mass | 8% by mass | 10% by mass | 15% by mass |
| GSSG residual ratio after storage at 60° C. for 1 week | 94% | 88% | 85% | 69% |

It was confirmed that the moisture content of the invention product would influence the storage stability.

Example 6: Confirmation of pH Stability of the Controlled-Release Oxidized Glutathione Preparation 1. Test Method pH stability of the invention product was evaluated in the manner described below.

Distilled water (25 ml) and 0.25 g of the invention product were introduced into a 50-ml centrifuge tube (Iwaki). With the use of an ultrasonic cleaner (SND Co., Ltd.), an ultrasonic wave of 38 kHz and 300 W was applied for 10 minutes. Thereafter, an adequate amount of an aqueous solution comprising 1 N hydrochloric acid and 1 N sodium hydroxide was added to adjust pH levels of aqueous phases in the centrifuge tube at 25° C. to 1, 2, 4, 6, 8, and 9, and the resultants were allowed to stand in an incubator at 60° C. for 3 days. The amount of oxidized glutathione in an aqueous phase in the centrifuge tube was measured via HPLC immediately after pH adjustment (0 hours after the initiation of storage) and 3 days after the initiation of storage. The proportion of the amount of oxidized glutathione in an aqueous phase 3 days after the initiation of storage relative to the amount of oxidized glutathione in an aqueous phase immediately after the pH adjustment was designated as the residual ratio (%).

2. Results

The results are shown in Table 6.

TABLE 6

| Item | pH level of Invention product when dispersed in water | | | | | |
|---|---|---|---|---|---|---|
| | 1 | 2 | 4 | 6 | 8 | 9 |
| GSSG residual ratio after storage at 60° C. for 3 days | 72% | 88% | 92% | 90% | 85% | 60% |

It was confirmed that a pH level of the invention product dispersed in water would influence the stability.

All publications, patents, and patent applications cited herein are incorporated herein by reference in their entirety.

Although embodiments of the disclosure have been described using specific terms, devices, and methods, such description is for illustrative purposes only. The words used are words of description rather than limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the preferred versions contained therein.

What is claimed is:

1. A controlled-release fertilizer comprising:
   0.000001% to 20% by mass of oxidized glutathione;
   0.01% to 20% by mass of carboxymethyl cellulose or a salt thereof; and
   60% to 99.98% by mass of an inorganic porous material.

2. The controlled-release fertilizer according to claim 1, wherein a pH level is from 2.0 to less than 8.0 when the controlled-release fertilizer is dispersed in water.

3. The controlled-release fertilizer according to claim 1, wherein the controlled-release fertilizer has a moisture content of 10% by mass or less.

4. The controlled-release fertilizer according to claim 1, wherein the oxidized glutathione is selected from the group consisting of an ammonium salt, a calcium salt, and a magnesium salt of oxidized glutathione.

5. The controlled-release fertilizer according to claim 1, wherein the oxidized glutathione is dispersed in a matrix comprising the carboxymethyl cellulose or a salt thereof.

6. The controlled-release fertilizer according to claim 1, obtained by a method comprising:
   preparing a mixture of the oxidized glutathione, the carboxymethyl cellulose or a salt thereof, and a medium, wherein the medium is water or a water-soluble medium; and
   forming grains comprising the oxidized glutathione and the carboxymethyl cellulose or a salt thereof from the mixture.

7. The controlled-release fertilizer according to claim 1, wherein a total mass of the oxidized glutathione eluted into distilled water at 30° C. is 0.60 T or less after 12 hours, 0.80 T or less after 24 hours, 0.90 T or less after 48 hours, and 0.95 T or less after 72 hours, when 1.25 g of the controlled-release fertilizer is added to 25 ml of the distilled water, provided that the initial total mass of the oxidized glutathione expressed in terms of the free form contained in the controlled-release fertilizer is designated as T.

8. A method for growing a plant, comprising applying a controlled-release fertilizer to the plant,
   wherein the controlled-release fertilizer comprises:
   0.000001% to 20% by mass of oxidized glutathione;
   0.01% to 20% by mass of carboxymethyl cellulose or a salt thereof; and
   60% to 99.98% by mass of an inorganic porous material.

9. The controlled-release fertilizer according to claim 1, wherein the inorganic porous material is clay.

10. The controlled-release fertilizer according to claim 1, wherein the controlled-release fertilizer comprises:
    0.005% to 5% by mass of the oxidized glutathione;
    0.1% to 10% by mass of the carboxymethyl cellulose or a salt thereof; and 80% to 99% by mass of the inorganic porous material.

11. The method according to claim 8, wherein the inorganic porous material is clay.

* * * * *